United States Patent
Nakabayashi et al.

(10) Patent No.: US 10,470,989 B2
(45) Date of Patent: Nov. 12, 2019

(54) SURFACE-TREATED POWDER USING THEANINE, AND COSMETIC PREPARATION CONTAINING SAME

(71) Applicant: KOSE CORPORATION, Chuo-ku (JP)

(72) Inventors: Hiromi Nakabayashi, Tokyo (JP); Yuji Masubuchi, Saitama (JP); Kaori Matsumoto, Tokyo (JP)

(73) Assignee: KOSE CORPORATION, Chuo-ku (JP)

( * ) Notice: Subject to any disclaimer, the term of this patent is extended or adjusted under 35 U.S.C. 154(b) by 55 days.

(21) Appl. No.: 15/036,114

(22) PCT Filed: Nov. 14, 2014

(86) PCT No.: PCT/JP2014/080172
§ 371 (c)(1),
(2) Date: May 12, 2016

(87) PCT Pub. No.: WO2015/072540
PCT Pub. Date: May 21, 2015

(65) Prior Publication Data
US 2016/0271032 A1    Sep. 22, 2016

(30) Foreign Application Priority Data

Nov. 15, 2013  (JP) .................................. 2013-237445
Nov. 15, 2013  (JP) .................................. 2013-237446

(51) Int. Cl.
| | | |
|---|---|---|
| *A61K 8/42* | (2006.01) |
| *A61Q 1/02* | (2006.01) |
| *A61K 8/29* | (2006.01) |
| *A61Q 1/10* | (2006.01) |
| *A61K 8/25* | (2006.01) |
| *A61K 8/88* | (2006.01) |
| *A61K 8/81* | (2006.01) |
| *A61K 8/891* | (2006.01) |
| *A61K 8/02* | (2006.01) |
| *A61K 8/19* | (2006.01) |
| *A61K 8/44* | (2006.01) |
| *A61Q 17/04* | (2006.01) |
| *A61Q 19/00* | (2006.01) |

(52) U.S. Cl.
CPC ................ *A61K 8/42* (2013.01); *A61K 8/022* (2013.01); *A61K 8/19* (2013.01); *A61K 8/25* (2013.01); *A61K 8/29* (2013.01); *A61K 8/44* (2013.01); *A61K 8/8147* (2013.01); *A61K 8/88* (2013.01); *A61K 8/891* (2013.01); *A61Q 1/02* (2013.01); *A61Q 1/10* (2013.01); *A61Q 17/04* (2013.01); *A61Q 19/00* (2013.01); *A61K 2800/612* (2013.01); *A61K 2800/622* (2013.01); *A61K 2800/651* (2013.01)

(58) Field of Classification Search
None
See application file for complete search history.

(56) References Cited

U.S. PATENT DOCUMENTS

| | | | | |
|---|---|---|---|---|
| 2001/0031271 | A1* | 10/2001 | Avalle | A61K 8/11 424/401 |
| 2007/0128311 | A1* | 6/2007 | Prakash | A23L 2/52 426/3 |
| 2007/0207101 | A1* | 9/2007 | Butts | A61K 8/19 424/63 |
| 2008/0254189 | A1* | 10/2008 | Mavroudis | A23F 3/163 426/597 |
| 2010/0317736 | A1* | 12/2010 | Shin | A61K 8/44 514/563 |

FOREIGN PATENT DOCUMENTS

| | | | |
|---|---|---|---|
| JP | 1-172312 | A | 7/1989 |
| JP | 1-50202 | B2 | 10/1989 |
| JP | 3-200879 | A | 9/1991 |
| JP | 5-229938 | A | 9/1993 |
| JP | 5-339518 | A | 12/1993 |
| JP | 9-202726 | A | 8/1997 |
| JP | 9-286715 | A | 11/1997 |
| JP | 9-328413 | A | 12/1997 |
| JP | 10-167931 | A | 6/1998 |
| JP | 10-218725 | A | 8/1998 |
| JP | 10-226626 | A | 8/1998 |
| JP | 11-335227 | A | 12/1999 |
| JP | 2000-302644 | A | 10/2000 |
| JP | 2001-72527 | A | 3/2001 |
| JP | 2003-183129 | A | 7/2003 |
| JP | 2003183129 | A * | 7/2003 |
| JP | 2004-43428 | A | 2/2004 |

(Continued)

OTHER PUBLICATIONS

English language translation of JP2003183129A.*
International Search Report dated Feb. 3, 2015 in PCT/JP2014/080172 filed Nov. 14, 2014.

*Primary Examiner* — Bethany P Barham
*Assistant Examiner* — Dominic Lazaro
(74) *Attorney, Agent, or Firm* — Oblon, McClelland, Maier & Neustadt, L.L.P.

(57) ABSTRACT

The present invention has an object to develop a surface-treated powder which shows both of smooth touch during application and good compatibility with skin, and to provide a cosmetic preparation which shows smooth touch during application as well as good compatibility with skin, and is excellent in cosmetic-film uniformity and in cosmetic retentivity by incorporating the treated powder into the cosmetic preparation. The powder for cosmetic preparation resolving the problem is characterized by being surface-treated with theanine.

18 Claims, No Drawings

(56) References Cited

FOREIGN PATENT DOCUMENTS

| | | |
|---|---|---|
| JP | 2007-204417 A | 8/2007 |
| JP | 2007-302800 A | 11/2007 |
| JP | 2014-240479 A | 12/2014 |
| WO | WO 2011/048757 | 4/2011 |

\* cited by examiner

SURFACE-TREATED POWDER USING THEANINE, AND COSMETIC PREPARATION CONTAINING SAME

TECHNICAL FIELD

The present invention relates to a theanine-surface-treated powder showing smooth touch and good compatibility with skin, and a cosmetic preparation obtained by using the same which shows smooth use feeling and good adhesion to skin and is excellent in uniformity of cosmetic-film and in cosmetic retentivity over time.

BACKGROUND ART

Into a cosmetic preparation, various powders such as an inorganic powder, an organic powder, and a coloring powder are incorporated for the purpose of providing a make-up effect and retentivity thereof and adjusting the touch. However, since inorganic powders are especially poor in compatibility with skin due to a nature of inorganics, a cosmetic preparation with an inorganic powder incorporated therein is poor in spreading on skin and gives strong squeaky feel, whereby physical irritation to skin is caused and smoothness during application is impaired. Furthermore, because of high aggregation property and low oil dispersibility of the particles, an inorganic powder has lowered long-term storage stability, make-up effect, UV absorption effect, and the like of the cosmetic preparation. For solving the problems, the surface of the powder has conventionally been treated with various surface treating agents. For example, a number of methods such as methods of surface treatment with an ester oil, a metal soap, lecithin, a silicone oil (see, for example, PTLs 1 and 2), a perfluoroalkyl oil (see, for example, PTLs 3 and 4), and the like are known.

However, although a powder surface-treated with an ester oil, a metal soap, a silicone oil, a perfluoroalkyl oil, and the like has smooth touch and is lowered in physical irritation to skin, such a powder is poor in affinity with a living body, and therefore has not been satisfactory in compatibility with skin. In addition, in order to achieve good touch and enhance the compatibility with skin, techniques of using an acylated amino acid (see, for example, PTLs 5 and 6) and techniques of using an acylated polypeptide obtained by acrylating a polypeptide which is a polymer of an amino acid (see, for example, PTLs 7 and 8) are known, but the effects thereof have not been satisfactory.

Although a cosmetic preparation which has good usability and touch and also shows high cosmetic retentivity has been conventionally demanded, it is not easy to satisfy both the requirements. In particular, in a powdery cosmetic preparation, when it is intended to enhance too much the adhesion to skin in pursuit of cosmetic retentivity, the powdery cosmetic preparation has a tendency to reduce smooth spreading and deteriorate usability and use feeling. In addition, uniform formation of cosmetic-film is also required, but it is difficult in practice to provide a cosmetic preparation satisfying all the requirements.

Among the demands of consumers regarding the cosmetic retentivity, there is a demand to prevent elimination of cosmetic-film due to secondary adhesion (a phenomenon that the cosmetic-film is broken up and eliminated due to a hand, handkerchief and face mask coming into contact with skin after application of the cosmetic preparation). However, in a cosmetic preparation which is enhanced merely in adhesion to skin, it has been difficult to also prevent the adhesion to hands or clothes. In order to prevent the secondary adhesion, for example, a technique of using an organic silicone resin (PTL 9), a technique of using a powder surface-treated with a specific film forming agent (PTL 10), and a technique of incorporating a boron nitride powder and a coating agent (PTL 11) are known. The techniques are however not fully satisfactory in the effect and the touch in use.

CITATION LIST

Patent Literature

PTL 1: JP-A-5-339518
PTL 2: JP-A-2001-072527
PTL 3: JP-A-10-167931
PTL 4: JP-A-11-335227
PTL 5: JP-A-1-50202
PTL 6: JP-A-3-200879
PTL 7: JP-A-10-226626
PTL 8: JP-A-9-328413
PTL 9: JP-A-10-218725
PTL 10: JP-A-2007-302800
PTL 11: JP-A-2000-302644

SUMMARY OF INVENTION

Technical Problem

An object of the present invention is to provide a novel surface-treated powder showing smooth touch and good compatibility with skin, a cosmetic preparation which shows smooth touch during application and good compatibility with skin and is excellent in uniformity of cosmetic-film and cosmetic retentivity, and a cosmetic preparation which is further excellent in preventing elimination of cosmetic-film due to secondary adhesion.

Solution to Problem

As a result of intensive studies in view of the above situation, the present inventors have found that among amino acid derivatives, theanine has a higher affinity with keratin which is a constituent of skin, and by performing surface treatment of powder using theanine, touch during application and skin compatibility are improved; and that, by incorporating the powder surface-treated with theanine into a cosmetic preparation, a cosmetic preparation which shows smooth spreading during application, and is excellent in compatibility with skin, and also excellent in uniformity of cosmetic-film and cosmetic retentivity can be obtained. The present inventors have further found that by combining an organic powder with the inorganic powder surface-treated with theanine, a powdery cosmetic preparation which is improved in smoothness of spreading during application, uniformity of cosmetic-film, and cosmetic retentivity over time, and is also excellent in the effect of preventing elimination of cosmetic-film due to secondary adhesion can be obtained, thereby completing the present invention.

That is, the present invention relates to a powder for a cosmetic preparation, the powder being surface-treated with theanine.

The present invention also relates to a cosmetic preparation having the surface-treated powder incorporated therein.

The present invention also relates to a powdery cosmetic preparation containing an inorganic powder surface-treated with theanine and an organic powder.

The present invention further relates to a powdery cosmetic preparation containing boron nitride together with an inorganic powder surface-treated with theanine and an organic powder.

Advantageous Effects of Invention

Theanine which is used in the present invention is excellent in affinity with keratin which is a constituent of skin, and therefore enhances compatibility with skin of a powder even with a small treatment amount and gives smooth touch. Accordingly, a cosmetic preparation in which the powder surface-treated with theanine is incorporated is excellent in compatibility with skin, shows smooth spreading and has good usability, and is further excellent in uniformity of cosmetic-film and cosmetic retentivity effect. In addition, a powdery cosmetic preparation in which an inorganic powder surface-treated with theanine is combined with an organic powder is improved in smoothness of spreading during application, uniformity of cosmetic-film, and cosmetic retentivity over time, and is further excellent in the effect of preventing elimination of cosmetic-film due to secondary adhesion.

DESCRIPTION OF EMBODIMENTS (Surface Treating Agent)

Theanine which is used in the present invention has a chemical name of glutamic acid-γ-monoethylamide and has a d-form and an l-form, and although the l-form generally exists, the present invention may include the d-form. When theanine was compared with various amino acid derivatives in the affinity with keratin by using a method of measuring the wavenumber shift in an ATR analysis, a shift to a lower wavenumber was observed on the hydrogen bond. Examples of commercial products of theanine include L-THEANINE (manufactured by Kurita Water Industries Co., Ltd.) and SUNTHEANINE (manufactured by Taiyo Kagaku Co., Ltd.).

(Surface-treated Powder for Cosmetic Preparation)

The surface-treated powder of the present invention is obtained by allowing theanine as mentioned above to be supported on the surface of a powder. The powder which is surface-treated is not particularly limited in the shape such as a sphere shape, a tabular shape, and a needle shape, the particle size such as an atomized form, a fine particle form, and a pigment grade, the particle structure such as a porous structure and non-porous structure, and the like, as long as the powder is a powder generally used for a cosmetic preparation. One kind or two or more kinds of an inorganic powder, a photoluminescent powder, an organic powder, an organic coloring powder, a complex powder, and the like may be used, but an inorganic powder such as an inorganic powder, a photoluminescent inorganic powder, and a complex inorganic powder is preferred, and an inorganic tabular powder and a metal oxide pigment such as titanium oxide, zinc oxide, and iron oxide are more preferred.

As the inorganic powder, one kind or two or more kinds selected from titanium oxide, black titanium oxide, iron blue pigment, ultramarine blue, colcothar, yellow iron oxide, black iron oxide, zinc oxide, aluminum oxide, silica, magnesium oxide, zirconium oxide, magnesium carbonate, calcium carbonate, chromium oxide, chromium hydroxide, carbon black, aluminum silicate, magnesium silicate, aluminum magnesium silicate, mica, synthetic mica, sericite, talc, kaolin, silicon carbide, barium sulfate, bentonite, smectite, boron nitride, and the like may be used. Incidentally, fine particles of approximately from 10 to 80 nm prepared from the powder may be used.

As the photoluminescent inorganic powder, one kind or two or more kinds selected from bismuth oxychloride, a titanium oxide-coated mica, an iron oxide-coated mica, an iron oxide-coated mica titanium, a titanium oxide-coated glass powder, an aluminum powder, and the like may be used. The photoluminescent inorganic powder may include in a part thereof an organic compound, but a part or the whole of the surface is preferably coated with an inorganic compound.

As the organic powder, one kind or two or more kinds selected from a nylon powder, a polymethyl methacrylate powder, an (acrylonitrile/methacrylic acid) copolymer powder, a (vinylidene chloride/methacrylic acid) copolymer powder, a PET resin powder, a polyethylene powder, a polystyrene powder, an organopolysiloxane elastomer powder, a polymethylsilsesquioxane powder, a polyurethane powder, a wool powder, a silk powder, a crystalline cellulose powder, an N-acyl lysine powder, and the like may be used.

As the coloring powder, one kind or two or more kinds selected from an organic tar pigment, an organic coloring rake pigment, and the like may be used.

As the complex inorganic powder, one kind or two or more kinds selected from a fine particle titanium oxide-coated mica titanium, a fine particle zinc oxide-coated mica titanium, a barium sulfate-coated mica titanium, a titanium oxide-containing silica, a zinc oxide-containing silica, and the like may be used. The complex inorganic powder may include an organic compound in a part thereof, but a part or the whole of the surface is preferably coated with an inorganic compound.

Among them, especially suitable as the powder to be surface-treated are a tabular inorganic powder such as talc and mica and a metal oxide pigment such as titanium oxide, zinc oxide, and iron oxide. In the case of, for example, titanium oxide, in particular, of fine particles, the powder is easily aggregated in the untreated state, but when the theanine mentioned above is used as a surface treating agent, since the dispersibility of the surface-treated titanium oxide is improved, it is possible to efficiently impart a UV blocking effect which is a characteristic of titanium oxide to a cosmetic preparation.

(Method for Producing Surface-treated Powder)

In the present invention, as the method for surface-treating powder, a known treatment method which has been conventionally used for modifying a powder used in a cosmetic preparation can be employed. For example, a wet method using a solvent, a dry method of treating powder in a gas phase, a mechanochemical method involving pulverization with mixing and shear, and the like may be used, and use of an aqueous solvent is particularly preferred since the surface treatment is then homogenously achieved. Specifically, the surface-treated powder can be obtained by dissolving theanine in water of 50° C., adding a powder in the aqueous solution, mixing the mixture uniformly with stirring using a Henschel mixer or the like mixer, and then drying and pulverizing the powder.

The surface-treated powder of the present invention may further be multiply coated before use with a generally known surface treating agent such as a silicone compound, a fluorine compound, an oil, a fat, a higher alcohol, a wax, a polymer, and a resin, for the purpose of improving dispersibility in the cosmetic preparation base, improving the touch, and the like.

The treatment amount of theanine in the surface-treated powder obtained as above is not particularly limited, but preferably 0.002 to 20% by mass (hereinafter abbreviated as "%" simply), more preferably 0.1 to 5%, in the treated powder. Within this range, a powder for a cosmetic preparation showing excellent touch and skin compatibility is obtained, and by incorporating the powder, a cosmetic preparation which spreads smoothly during application, is excellent in compatibility with skin, and also excellent in uniformity of cosmetic-film and cosmetic retentivity can be obtained.

The surface-treated powder of the present invention is obtained by allowing theanine mentioned above to be supported on the surface of a powder. The mode of the support in the present invention is not particularly limited, and theanine may be supported on the surface of a powder in a particle form or may be supported in a film form together with other components. In addition, theanine may be supported on the surface of a powder by physically adhering, or may be supported by chemical binding, and may be supported not on the whole but on a part of the surface of a powder.

(Cosmetic Preparation)

The cosmetic preparation of the present invention is produced by combining and blending one kind or two or more kinds of the surface-treated powders as described above with known components of a cosmetic preparation according to an ordinary method. The amount of the surface-treated powders incorporated in the cosmetic preparation of the present invention is not particularly limited and different depending on the formulation form and the item of the cosmetic preparation, but the amount may be 0.1 to 90%, preferably 5 to 40%.

In the cosmetic preparation, components capable of being incorporated may be incorporated appropriately as need arises. For example, an oil, a surfactant, an alcohol, water, a moisturizer, a gelling agent, and a thickener, a powder other than the surface-treated powder, a UV absorber, a preservative, a antimicrobial an antioxidant, a component for beautiful skin (a whitening agent, a cell activator, an anti-inflammatory agent, a blood circulation promoter, a skin astringent, an antiseborrheic agent, etc.), a vitamin, an amino acid, a nucleic acid, a hormone, and the like may be incorporated.

Examples of the formulation form of the cosmetic preparation of the present invention include a powder formulation, an oil-in-water emulsion formulation, a water-in-oil emulsion formulation, an oily formulation, an aqueous formulation, and a solvent formulation. Examples of the form of the cosmetic preparation include a powder form, a powdery solid form, an oily solid form, a cream form, a gel form, a liquid form, a mousse from, and a spray from. Among them, a powder formulation is particularly preferred since it can maximize the characteristics of the surface-treated powder of the present invention. The cosmetic preparation of the present invention is required only to contain the surface-treated powder of the present invention, and can be suitably used especially for a makeup cosmetic preparation such as a foundation, a concealer, a face powder, an eyeshadow, a cheek rouge, a makeup base, an eye color, a rouge, an eyebrow, a mascara, an eyeliner, and a manicure, and for a sun screen cosmetic preparation.

(Powdery Cosmetic Preparation)

A cosmetic preparation especially suitable as the cosmetic preparation of the present invention is a powdery cosmetic preparation in which an organic powder is incorporated together with inorganic powder surface-treated with theanine.

The inorganic powder surface-treated with theanine for use in the powdery cosmetic preparation of the present invention is the powder for a cosmetic preparation described above in which an inorganic powder is used as the powder to be treated.

Theanine which is used as the surface treating agent has a chemical name of glutamic acid-γ-monoethylamide and has a d-form and an l-form, and although the l-form generally exists, the present invention may include the d-form. When theanine was compared with various amino acid derivatives in the affinity with keratin by using a method of measuring the wavenumber shift in an ATR analysis, a shift to a lower wavenumber was observed on the hydrogen bond. Examples of commercial products of theanine include L-THEANINE (manufactured by Kurita Water Industries Co., Ltd.) and SUNTHEANINE (manufactured by Taiyo Kagaku Co., Ltd.).

The inorganic powder to be surface-treated is not particularly limited in the shape such as a sphere shape, a tabular shape, and a needle shape, the particle size such as an atomized form, a fine particle form, and a pigment grade, the particle structure such as a porous structure and a non-porous structure, and the like, as long as it is an inorganic powder generally used in a cosmetic preparation, and one kind or two or more kinds of an inorganic powder, a photoluminescent inorganic powder, a complex inorganic powder, and the like may be used.

As the inorganic powder, one kind or two or more kinds selected from titanium oxide, black titanium oxide, iron blue pigment, ultramarine blue, colcothar, yellow iron oxide, black iron oxide, zinc oxide, aluminum oxide, silica, magnesium oxide, zirconium oxide, magnesium carbonate, calcium carbonate, chromium oxide, chromium hydroxide, carbon black, aluminum silicate, magnesium silicate, aluminum magnesium silicate, mica, synthetic mica, sericite, talc, kaolin, silicon carbide, barium sulfate, bentonite, smectite, boron nitride, and the like may be used. Incidentally, fine particles of approximately from 10 to 80 nm prepared from the powder may be used.

Examples of the photoluminescent inorganic powder include bismuth oxychloride, a titanium oxide-coated mica, an iron oxide-coated mica, an iron oxide-coated mica titanium, a titanium oxide-coated glass powder, and an aluminum powder. The photoluminescent inorganic powder may include an organic compound in part thereof, but a part or the whole of the surface is preferably coated with an inorganic compound.

Examples of the complex inorganic powder include a fine particle titanium oxide-coated mica titanium, a fine particle zinc oxide-coated mica titanium, a barium sulfate-coated mica titanium, a titanium oxide-containing silica, and a zinc oxide-containing silica. The complex inorganic powder may include an organic compound in part thereof, but in this case, a part or the whole of the surface is preferably coated with an inorganic compound.

Among them, especially suitable as the powder to be surface-treated of the present invention are a tabular inorganic powder such as talc and mica and a metal oxide pigment such as titanium oxide, zinc oxide, and iron oxide. In the case of, for example, titanium oxide, especially of fine particles, the powder is easily aggregated in the untreated state, but when the theanine mentioned above is used as a surface treating agent, since the dispersibility of the surface-treated titanium oxide is improved, it is possible to efficiently impart a UV blocking effect which is a characteristic of titanium oxide to the cosmetic preparation.

As for the method of the surface treatment in the surface-treated powder used in the present invention, a known treatment method which has been conventionally used for modifying a powder used in a cosmetic preparation can be employed. Examples thereof include a wet method using a solvent, a dry method of treating powder in a gas phase, and a mechanochemical method involving pulverization with mixing and shear may be used, and use of an aqueous solvent is particularly preferred since the surface treatment is then homogenously achieved. Specifically, the surface-treated powder can be obtained by dissolving theanine in water of 50° C., adding a powder in the aqueous solution, mixing the mixture uniformly with stirring using a Henschel mixer or the like mixer, and then drying and pulverizing the powder.

The surface-treated powder used in the present invention is one in which the theanine described above is supported on the surface of the inorganic powder described above, and the mode of the support is not particularly limited, and, for example, theanine may be supported on the surface of a powder in a particle form or may be supported in a film form together with other components. Theanine may be supported on the surface of a powder by physically adhering, or may be supported by chemical binding, and may be supported not on the whole but on a part of the surface of a powder.

The treatment amount of theanine is not particularly limited, but preferably 0.002 to 20%, more preferably 0.1 to 5%, in the surface-treated powder. When the treatment amount is within this range, a surface-treated powder having excellent affinity with skin is obtained, and a cosmetic preparation having the powder incorporated therein is favorable in the touch.

The content of the inorganic powder surface-treated with theanine in the powdery cosmetic preparation of the present invention is not particularly limited, but preferably 0.1 to 90%, further preferably 1 to 40%. When the inorganic powder is used within the range, the affinity with skin of the surface-treated powder itself is efficiently exhibited. In the case of being combined with an organic powder to produce a powdery cosmetic preparation, the effect of preventing elimination of cosmetic-film due to secondary adhesion (hereinafter, abbreviated to "secondary adhesion-less effect") is increased, and therefore the case is preferred.

On the other hand, the organic powder used in the powdery cosmetic preparation of the present invention is not particularly limited in the shape such as a sphere shape and a tabular shape, the particle size such as a fine particle form, the particle structure such as a porous structure and non-porous structure, and the like, as long as the powder is an organic powder generally used in a cosmetic preparation. Specifically, one kind or two or more kinds of a nylon powder, a poly(methyl methacrylate) powder, poly(alkyl acrylate) powder, an (acrylonitrile/methacrylic acid) copolymer powder, a (vinylidene chloride/methacrylic acid) copolymer powder, a PET resin powder, a polyethylene powder, a polystyrene powder, an organopolysiloxane elastomer powder, a polymethylsilsesquioxane powder, a polyurethane powder, a wool powder, a silk powder, a crystalline cellulose powder, an N-acyllysine powder, and the like may be used. Among them, a nylon powder, a poly(methyl methacrylate) powder, a crystalline cellulose powder, and an organopolysiloxane elastomer powder are preferred since these organic powders spread smoothly and are excellent in use feeling when combined with the theanine-surface-treated inorganic powder.

The content of the organic powder in the powdery cosmetic preparation of the present invention is not particularly limited, and is preferably 0.1 to 30%, and more preferably 5 to 20%. Within the range, the organic powder deposits on the outer side of the theanine-surface-treated powder layer oriented in the vicinity of the surface of the skin and exhibits a barrier effect against hands and clothes, thereby enhancing the secondary adhesion-less effect.

The powdery cosmetic preparation of the present invention preferably further contains boron nitride. The boron nitride for use in the present invention is not limited in the crystal structure as long as it is a boron nitride which is used in a common cosmetic preparation, and those having any crystal structure such as hexagonal crystal and cubic crystal may be used. The mean particle size thereof is not particularly limited, but preferably approximately from 1 to 200 µm, more preferably approximately from 5 to 20 µm. The content thereof is also not particularly limited, but preferably approximately from 0.1 to 30%, further preferably approximately from 0.5 to 5%. Within the ranges, the lubricity of the boron nitride further enhances the uniformity of the cosmetic-film, and therefore the cosmetic retentivity and the secondary adhesion-less effect are synergistically enhanced. Incidentally, the mean particle size is a value which is measured by a laser diffraction/scattering particle size distribution analyzer (HORIBA LA-950 PARTICLE ANALYZER).

Into the powdery cosmetic preparation of the present invention, in addition to the above components, components which can be incorporated in a common cosmetic preparation may be appropriately incorporated as required to the extent that does not impair the effects of the present invention.

Specifically, for example, a powder other than the surface-treated powder and the organic powder described above, an oil, a surfactant, an alcohol, water, a moisturizer, a UV absorber, a preservative, an antimicrobial agent, an antioxidant, a cosmetic component (a whitening agent, a cell activator, an anti-inflammatory agent, a blood circulation promoter, a skin astringent, an antiseborrheic agent, a vitamin, an amino acid, etc.) may be incorporated.

As the attribute of the powdery cosmetic preparation of the present invention, a powder form and a powdery solid form may be mentioned.

The production method thereof is not particularly limited, and, for example, the inorganic powder surface-treated with theanine, an organic powder, and other powders to be incorporated as required are mixed and dispersed together, and an oil or the like is added as required to uniformly disperse the mixture. The mixture is charged as it is in a container, whereby a powdery cosmetic preparation can be obtained. In the case of a powdery solid form, a method in which the mixture is charged and molded in a dish container made of a metal or a resin (dry compaction molding) and a method in which the mixture is dispersed in a solvent in advance and then charged in a container, and dried and molded (wet molding) may be exemplified.

In addition, examples of the powdery cosmetic preparation of the present invention may include a makeup cosmetic preparation such as a foundation, a concealer, a face powder, an eyeshadow, and a cheek rouge.

EXAMPLES

Next, the present invention will be described in more detail with reference to examples, but the present invention is by no means limited thereto.

(Production Examples of Surface-treated Powder)

A surface-treated powder was prepared using theanine as a surface treating agent according to the following method.

Production Example 1

Example of Titanium Oxide

To 49.0 g of titanium oxide (TIPAQUE CR-50: manufactured by Ishihara Sangyo Kaisha, Ltd.) or fine particle titanium oxide (MT-500SA: manufactured by Tayca Corporation), a solution of 1.0 g of theanine as a surface treating agent dissolved in 70 g of water was added and mixed. The mixture was dried in air and pulverized with a pulverizer, thereby obtaining a 2.0%-treated titanium oxide.

Production Example 2

Example of Iron Oxide

As in the above, to 47.5 q of red iron oxide (TAROX R-516P: manufactured by Titan Kogyo, Ltd.), yellow iron oxide (TAROX IRON OXIDE YP1200P: manufactured by Titan Kogyo, Ltd.), or black iron oxide (TAROX BLACK BL-100P: manufactured by Titan Kogyo, Ltd.), a solution of 2.5 g of theanine as a surface treating agent dissolved in 70 g of water was added and mixed, and the mixture was dried in air and pulverized with a pulverizer, thereby obtaining a 5.0%-treated iron oxide.

Production Example 3

Example of Talc, Mica, or Sericite

As in the above, to 49.5 g of talc (TALC JA-46R: manufactured by Asada Milling, Co., Ltd.), mica (MICA POWDER TM-20: manufactured by YAMAGUCHI MICA Co., Ltd.), or sericite (SERICITE FSE: manufactured by Sanshin Ko Kogyo), a mixed liquid of 0.5 g of theanine as a surface treating agent dissolved in 70 g of water was added and mixed, and the mixture was dried in air and pulverized with a pulverizer, thereby obtaining a 1.0%-treated powder.

Production Example 4

To 49.0 g of sericite (SERICITE FSE: manufactured by Sanshin Ko Kogyo), a solution of 1.0 g of theanine as a surface treating agent dissolved in 70 g of water was added and mixed, and the mixture was dried in air and pulverized with a pulverizer, thereby obtaining a theanine (2%)-treated sericite.

Production Example 5

According to the Production Example 4, theanine was added to each of various powders in an amount to give a treatment amount (X %), thereby obtaining a theanine (X %)-treated powder.

Comparative Production Example 1

Examples of Methyl Hydrogen Polysiloxane-treated Powder

The raw material powders of Production Examples 1 to 3 were each treated according to the Production Examples except that theanine and water were changed to methyl hydrogen polysiloxane (KF-99-P: manufactured by Shin-Etsu Chemical, Co., Ltd.), thereby obtaining powders surface-treated with methyl hydrogen polysiloxane.

Comparative Production Example 2

Examples of Stearoyl Glutamic Acid Salt-treated Powder

The raw material powders of Production Examples 1 to 3 were each treated according to the Production Examples except that theanine was changed to disodium stearoyl glutamate, thereby obtaining powders surface-treated with disodium stearoyl glutamate.

(Method for Evaluating Surface-treated Powder)

The theanine-treated powders obtained in Production Example 5 above were evaluated according to the following method.

[Evaluation Method]

On an inside portion of a upper arm of each of 10 panelists specializing in cosmetic evaluation, equal amounts of each untreated powder and treated powder obtained in Production Example 5 were placed, and the touch at the time of spreading the powders with a finger was evaluated. When another treated-powder was to be evaluated, the sample was once rinsed off before the next evaluation. The "smoothness" and "skin compatibility" in comparison with each untreated powder were evaluated by each panelist according to the following evaluation criteria, and in turn the average of the scores by all the panelists was used to make determination according to the following determination criteria.

(Evaluation Criteria)
(Evaluation Result): (Score)
Very good: 5
Good: 4
Normal: 3
Bad: 2
Very bad: 1
(Determination Criteria)
(Average of Scores): (Determination)
4.5 or higher: ⊚ Very good
4.0 or higher and lower than 4.5: ○ Good
3.0 or higher and lower than 4.0: Δ Satisfactory
Lower than 3.0: x Bad

TABLE 1

| Untreated powder | Evaluation item | Treatment amount (X %) | | | | | | | |
|---|---|---|---|---|---|---|---|---|---|
| | | 20 | 10 | 5 | 2 | 1 | 0.5 | 0.1 | 0.002 |
| Titanium oxide *1 | Smoothness | Δ | Δ | Δ | ○ | ⊚ | ⊚ | ⊚ | Δ |
| | Skin Compatibility | Δ | Δ | ○ | ○ | ⊚ | ⊚ | ⊚ | Δ |

TABLE 1-continued

| Untreated powder | Evaluation item | Treatment amount (X %) | | | | | | | |
|---|---|---|---|---|---|---|---|---|---|
| | | 20 | 10 | 5 | 2 | 1 | 0.5 | 0.1 | 0.002 |
| Red iron oxide *2 | Smoothness | Δ | Δ | ○ | ○ | ○○ | ○○ | ○○ | Δ |
| | Skin Compatibility | Δ | Δ | ○ | ○○ | ○○ | ○○ | ○○ | Δ |
| Sericite *3 | Smoothness | Δ | ○ | ○ | ○○ | ○○ | ○○ | ○ | Δ |
| | Skin Compatibility | Δ | ○ | ○○ | ○○ | ○○ | ○○ | ○ | Δ |

*1: TIPAQUE CR-50 (manufactured by Ishihara Sangyo Kaisha Ltd.)
*2: TAROX R-516P (manufactured by Titan Kogyo, Ltd.)
*3: SERICITE FSE (manufactured by Sanshin Ko Kogyo)

It was demonstrated that surface treatment with theanine allows any powder to show smoother touch during application and better skin compatibility as compared with the untreated powder, in a wide range of treatment amount.

(Formulation Examples of Cosmetic Preparation)

The surface-treated powders prepared by the above methods were used in the following formulations.

Examples 1 to 4 and Comparative Examples 1 to 3

Powder Foundation

Powder foundations of Examples 1 to 4 and Comparative Examples 1 to 3 were prepared according to the constitutions and production methods in Table 2. Each of the obtained powder foundations was evaluated for smooth use feeling, uniformity of cosmetic-film, cosmetic retentivity, and secondary adhesion-less effect, by the methods described below. The results are also shown in Table 2 together.

[Production Method]

A: Components 1 to 16 are mixed and dispersed.

B: Components 17 to 19 are added to A and the mixture is uniformly mixed.

C: B is pulverized with a pulverizer.

[Evaluation Method 1: Smooth Use Feeling, Uniformity of Cosmetic-film, Cosmetic Retentivity]

The samples of Examples and Comparative Examples above were evaluated by each of 20 panelists specializing in cosmetic evaluation for each of the items "smooth use feeling", "uniformity of cosmetic-film", and "cosmetic retentivity" according to the following 7-level evaluation criteria, and in turn the average of the scores by all the panelists was used to make determination according to the following determination criteria. Incidentally, as for the cosmetic retentivity, each panelist applied each sample on his/her face and then performed a normal life, and the cosmetic effect after 6 hours was evaluated in comparison with that immediately after the application.

TABLE 2

| | | (%) | | | | | | |
|---|---|---|---|---|---|---|---|---|
| | | Example | | | | Comparative Example | | |
| No | Component | 1 | 2 | 3 | 4 | 1 | 2 | 3 |
| 1 | Talc of Production Example 3 | 10 | 3 | 5 | — | — | — | — |
| 2 | Red iron oxide of Production Example 2 | — | — | — | 0.1 | — | — | — |
| 3 | Titanium oxide of Production Example 1 | — | — | — | 10 | — | — | — |
| 4 | Talc of Comparative Production Example 1 | — | — | — | — | 10 | — | — |
| 5 | Talc of Comparative Production Example 2 | — | — | — | — | — | 10 | — |
| 6 | Boron nitride | 10 | 10 | 10 | 10 | 10 | 10 | 10 |
| 7 | Talc | 24.4 | 4.4 | 29.4 | 34.4 | 24.4 | 24.4 | 34.4 |
| 8 | Sericite | 20 | 20 | 20 | 20 | 20 | 20 | 20 |
| 9 | Titanium oxide | 10 | 10 | 10 | — | 10 | 10 | 10 |
| 10 | Zinc oxide | 3 | 3 | 3 | 3 | 3 | 3 | 3 |
| 11 | Iron oxide | 0.1 | 0.1 | 0.1 | — | 0.1 | 0.1 | 0.1 |
| 12 | Nylon powder | 3 | 3 | 3 | 3 | 3 | 3 | 3 |
| 13 | Barium sulfate | 5 | 5 | 5 | 5 | 5 | 5 | 5 |
| 14 | Poly(methyl methacrylate) powder | 5 | 5 | 5 | 5 | 5 | 5 | 5 |
| 15 | (Vinyldimethicone/methicone silsesquioxane) crosspolymer | 0.5 | 0.5 | 0.5 | 0.5 | 0.5 | 0.5 | 0.5 |
| 16 | Squalane | 2 | 2 | 2 | 2 | 2 | 2 | 2 |
| 17 | 2-Ethylhexyl p-methoxycinnamate | 3 | 3 | 3 | 3 | 3 | 3 | 3 |
| 18 | Glyceryl tri(2-ethylhexanate) | 2 | 2 | 2 | 2 | 2 | 2 | 2 |
| 19 | Dimethyl polysiloxane (6 mm$^2$/s: 25° C.) | 2 | 2 | 2 | 2 | 2 | 2 | 2 |
| | Evaluation item and determination result | | | | | | | |
| i | Smooth use feeling | ○○ | ○○ | ○○ | ○ | ○ | ○○ | x |
| ii | Uniformity of cosmetic-film | ○○ | ○○ | ○ | ○ | Δ | Δ | x |
| iii | Cosmetic retentivity | ○○ | ○○ | ○○ | ○○ | Δ | Δ | x |
| iv | Secondary adhesion-less effect | ○○ | ○○ | ○○ | ○○ | x | x | x |

(Evaluation Criteria)
(Evaluation Result): (Score)
Very good: 6
Good: 5
Satisfactory: 4
Normal: 3
Slightly bad: 2
Bad: 1
Very bad: 0
(Determination Criteria)
(Average of Scores): (Determination)
5.0 or higher: ○○ Very good
3.5 or higher and lower than 5.0: ○ Good
1.5 or higher and lower than 3.5: Δ Bad
Lower than 1.5: x Very bad

[Evaluation 2: Secondary Adhesion-less Effect]

Each sample of Examples and Comparative Examples above was applied on the whole face and finished, and immediately after that, a facial tissue was pushed against a forehead portion. The coloring degree by the foundation which transferred to the facial tissue at that time was evaluated according to the following criteria.

(Evaluation Criteria)
(Evaluation Result): (Score)
Very good (not colored): 6
Good (hardly colored): 5
Reasonably good: 4
Normal (colored a little): 3
Slightly bad: 2
Bad (colored): 1
Very bad: 0
(Determination Criteria)
(Average of Scores): (Determination)
5.0 or higher: ○○ Very good
3.5 or higher and lower than 5.0: ○ Good
1.5 or higher and lower than 3.5: Δ Bad
Lower than 1.5: x Very bad

[Results]

The powder foundations of Examples 1 to 4 showed smooth touch during application as well as good adhesion to skin, and were excellent in the uniformity of cosmetic-film, the cosmetic retentivity, and the secondary adhesion-less effect. On the other hand, Comparative Examples 1 and 2 in which methyl hydrogen polysiloxane-treated powder or stearoyl glutamic acid salt-treated powder was used instead of the surface-treated powder of the present invention, and Comparative Example 3 in which the surface-treated powder of the present invention was not contained were poorer in each item.

Examples 5 to 9 and Comparative Example 4

Powder Foundation (Powder Form)

Powder foundations of Examples 5 to 9 and Comparative Example 4 were prepared according to the constitutions and production method shown in Table 3. Each of the obtained powder foundations was evaluated for the "smooth use feeling", "uniformity of cosmetic-film", "cosmetic retentivity", and "secondary adhesion-less effect" by the evaluation method described above. The results are also shown in Table 3 together.

TABLE 3

(%)

| No | Components | Example 5 | Example 6 | Example 7 | Example 8 | Example 9 | Comparative Example 4 |
|---|---|---|---|---|---|---|---|
| 1 | Theanine(2%)-treated sericite of Production Example 4 | 5 | 0.1 | 20 | 5 | 5 | — |
| 2 | Boron nitride | 3 | 3 | 3 | — | 3 | 3 |
| 3 | Mica | 20 | 24.9 | 5 | 20 | 32 | 25 |
| 4 | Iron oxide | 3 | 3 | 3 | 3 | 3 | 3 |
| 5 | Talc | 20 | 20 | 20 | 20 | 20 | 20 |
| 6 | Silica | 5 | 5 | 5 | 5 | 5 | 5 |
| 7 | Titanium oxide | 15 | 15 | 15 | 15 | 15 | 15 |
| 8 | Zinc oxide | 1 | 1 | 1 | 1 | 1 | 1 |
| 9 | Barium sulfate | 5 | 5 | 5 | 5 | 5 | 5 |
| 10 | Nylon powder | 5 | 5 | 5 | 5 | — | 5 |
| 11 | Poly(methyl methacrylate) powder | 5 | 5 | 5 | 5 | — | 5 |
| 12 | (Vinyl dimethicone/methicone silsesquioxane) crosspolymer | 2 | 2 | 2 | 2 | — | 2 |
| 13 | Squalane | 2 | 2 | 2 | 2 | 2 | 2 |
| 14 | 2-Ethylhexyl p-methoxycinnamate | 3 | 3 | 3 | 3 | 3 | 3 |
| 15 | Glyceryl tri(2ethylhexanoate) | 3 | 3 | 3 | 3 | 3 | 3 |
| 16 | Dimethyl polysiloxane (6 mm$^2$/s: 25° C.) | 3 | 3 | 3 | 3 | 3 | 3 |
| | Evaluation item and determination result | | | | | | |
| i | Smooth use feeling | ○○ | ○○ | ○ | ○ | ○ | ○ |
| ii | Uniformity of cosmetic-film | ○○ | ○○ | ○ | ○ | ○ | ○ |
| iii | Cosmetic retentivity | ○○ | ○ | ○○ | ○ | ○ | Δ |
| iv | Secondary adhesion-less effect | ○○ | ○ | ○○ | ○ | Δ | x |

[Production Method]
A: Components 1 to 12 are mixed and dispersed.
B: Components 13 to 16 are added to A and the mixture is uniformly mixed.
C: B is pulverized with a pulverizer.

[Results]

The powder foundations of Examples 5 to 9 showed smooth touch during application as well as good compatibility with skin, and were excellent in the uniformity of cosmetic-film, the cosmetic retentivity, and the secondary adhesion-less effect. This is inferred to be attributable to good lubricity of the organic powder and high affinity of the organic powder with theanine. Meanwhile, the results showed that Comparative Example was inferior in the cosmetic retentivity and the secondary adhesion-less effect.

Example 10

W/O Liquid Foundation

| (Components) | (%) |
| --- | --- |
| 1. Titanium oxide of Production Example 1 | 10.0 |
| 2. Red iron oxide of Production Example 2 | 0.4 |
| 3. Yellow iron oxide of Production Example 2 | 2.0 |
| 4. Black iron oxide of Production Example 2 | 0.1 |
| 5. Silica | 3.0 |
| 6. Lauryl PEG-9 polydimethylsiloxyethyl dimethicone | 1.0 |
| 7. Cyclomethicone | 5.0 |
| 8. PEG-9 Polydimethylsiloxyethyl dimethicone | 5.0 |
| 9. Methyl trimethicone | 20.0 |
| 10. Petrolatum | 1.0 |
| 11. 2-Ethylhexyl p-methoxycinnamate | 4.0 |
| 12. Phospholipid | 0.5 |
| 13. Sorbitan sesquiisostearate | 1.0 |
| 14. (Dimethicone/vinyl dimethicone) crosspolymer | 3.0 |
| 15. Isotridecyl isononanoate | 2.0 |
| 16. Glycerol | 2.0 |
| 17. Ethanol | 2.0 |
| 18. Sodium chloride | 0.5 |
| 19. Water | Balance |
| 20. Preservative | q.s. |
| 21. Perfume | q.s. |

[Production Method]
(1) Components 1 to 7 are uniformly dispersed with a roller.
(2) Components 8 to 15 and 21 are uniformly mixed.
(3) (1) is added to (2), and the mixture is uniformly mixed.
(4) Components 16 to 20 are added to (3), and the mixture is emulsified. A W/O foundation was thus obtained.

[Results]
The W/O foundation of the Example showed a smooth touch during application as well as good adhesion to skin, and was excellent in the uniformity of cosmetic-film and the cosmetic retentivity.

Example 11

W/O BB Cream

| (Components) | (%) |
| --- | --- |
| 1. Titanium oxide of Production Example 1 | 10.0 |
| 2. Zinc oxide of Production Example 1 | 3.0 |
| 3. Red iron oxide of Production Example 2 | 0.4 |
| 4. Yellow iron oxide of Production Example 2 | 2.0 |
| 5. Black iron oxide of Production Example 2 | 0.1 |
| 6. Lauroyl lysine | 3.0 |
| 7. Lauryl PEG-9 polydimethylsiloxyethyl dimethicone | 1.0 |
| 8. Dimethicone | 5.0 |
| 9. PEG-9 Dimethicone | 5.0 |
| 10. Liquid paraffin | 20.0 |
| 11. Inulin stearate | 0.5 |
| 12. Dextrin palmitate | 0.5 |
| 13. Cyclomethicone | 4.5 |
| 14. Dipentaerythrityl hexa(hydroxystearate/stearate/rosinate) | 1.0 |
| 15. (Dimethicone/vinyl dimethicone) crosspolymer | 3.0 |
| 16. Neopentylene glycol diethylhexanoate | 2.0 |
| 17. 2-Ethylhexyl p-methoxycinnamate | 2.0 |
| 18. Hexyl diethylaminohydroxybenzoylbenzoate | 2.0 |
| 19. BG | 8.0 |
| 20. Sodium chloride | 0.5 |
| 21. Water | Balance |

-continued

| (Components) | (%) |
| --- | --- |
| 22. Preservative | q.s. |
| 23. Perfume | q.s. |

[Production Method]
(1) Components 1 to 9 are uniformly dispersed with a roller.
(2) Components 10 to 12 are dissolved with mild heat.
(3) Components 13 to 18 are added to (1) and (2) and the mixture is uniformly mixed.
(4) Components 19 to 23 are added to (3) and the mixture is emulsified. A W/O BB cream was thus obtained.

[Results]
The W/O BB cream of the Example showed smooth touch during application as well as good adhesion to skin, and was excellent in the uniformity of cosmetic-film and the cosmetic retentivity.

Example 12

Oil Foundation

| (Components) | (%) |
| --- | --- |
| 1. Titanium oxide of Production Example 3 | 10.0 |
| 2. Red iron oxide of Production Example 2 | 0.4 |
| 3. Yellow iron oxide of Production Example 2 | 2.0 |
| 4. Black iron oxide of Production Example 2 | 0.1 |
| 5. Talc of Production Example 3 | Balance |
| 6. Lauroyl lysine | 1.0 |
| 7. (Vinyl dimethicone/methicone silsesquioxane) crosspolymer | 15.0 |
| 8. PEG-9 Dimethicone | 5.0 |
| 9. Cyclomethicone | 20.0 |
| 10. Dimethicone | 10.0 |
| 11. Isododecane | 1.0 |
| 12. (Acrylates/dimethicone) copolymer | 4.5 |
| 13. Isohexadecane | 1.0 |
| 14. (Dimethicone/(PEG-10/15)) crosspolymer | 3.0 |
| 15. Triethylhexanoin | 10.0 |
| 16. 2-Ethylhexyl p-methoxycinnamate | 7.0 |
| 17. Preservative | q.s. |
| 18. Perfume | q.s. |

[Production Method]
(1) Components 1 to 10 are uniformly dispersed with a roller.
(2) Components 11 to 16 are uniformly dissolved.
(3) (1) and Components 17 and 18 are added to (3) and the mixture is uniformly mixed. An oil foundation was thus obtained.

[Results]
The oil foundation of the Example showed smooth touch during application as well as good adhesion to skin, and was excellent in the uniformity of cosmetic-film and the cosmetic retentivity.

Example 13

O/W Liquid Foundation

| (Components) | (%) |
| --- | --- |
| 1. Polyoxyethylene sorbitan monooleate (20EO) | 0.5 |
| 2. Sorbitan sesquioleate | 0.5 |
| 3. 1,3-Butylene glycol | 10.0 |

-continued

| (Components) | (%) |
|---|---|
| 4. Titanium oxide of Production Example 1 | 10.0 |
| 5. Red iron oxide of Production Example 2 | 0.4 |
| 6. Yellow iron oxide of Production Example 2 | 2.0 |
| 7. Black iron oxide of Production Example 2 | 0.1 |
| 8. Talc of Production Example 3 | 5.0 |
| 9. Xanthan gum | 0.2 |
| 10. Carboxyvinyl polymer | 0.3 |
| 11. Triethanolamine | 1.0 |
| 12. Purified water | Balance |
| 13. Phenylbenzimidazole sulfonic acid | 2.0 |
| 14. Ethanol | 2.0 |
| 15. Stearic acid | 1.0 |
| 16. Behenyl alcohol | 0.5 |
| 17. Liquid paraffin | 2.0 |
| 18. Glyceryl tri(2-ethylhexanoate) | 2.0 |
| 19. 2-Ethylhexyl p-methoxycinnamate | 2.0 |
| 20. Petrolatum | 0.5 |
| 21. Preservative | q.s. |
| 22. Perfume | q.s. |

[Production Method]
(1) Components 1 to 8 are uniformly dispersed with a roller.
(2) Components 9 to 14 are uniformly mixed.
(3) (1) is added to (2) and uniformly mixed.
(4) Components 15 to 21 are mixed and dissolved at 80° C.
(5) (4) is added to (3) at 80° C. and the mixture is emulsified.
(6) (5) is cooled, and component 22 is added thereto. An O/W foundation was thus obtained.

[Results]
The O/W foundation of the Example showed smooth touch during application as well as good adhesion to skin, and was excellent in the uniformity of cosmetic-film and the cosmetic retentivity.

Example 14

Oily Solid Foundation

| (Components) | (%) |
|---|---|
| 1. Talc | 15.0 |
| 2. Mica | 10.0 |
| 3. Titanium oxide of Production Example 1 | 15.0 |
| 4. Red iron oxide of Production Example 2 | 1.0 |
| 5. Yellow iron oxide of Production Example 2 | 3.0 |
| 6. Black iron oxide of Production Example 2 | 0.2 |
| 7. Synthetic gold mica | 3.0 |
| 8. Nylon | 3.0 |
| 9. Polyethylene wax | 7.0 |
| 10. Microcrystalline wax | 6.0 |
| 11. Glyceryl tri(2-ethylhexanoate) | Balance |
| 12. Dimethyl polysiloxane | 10.0 |
| 13. Liquid paraffin | 10.0 |
| 14. Diisostearyl malate | 5.0 |
| 15. Lauryl PEG-9 polydimethylsiloxyethyl dimethicone | 2.0 |
| 16. Lauryl polyglyceryl-3 polydimethylsiloxyethyl dimethicone | 1.0 |
| 17. Trimethylsiloxycinnamic acid | 0.5 |
| 18. Cyclomethicone | 5.0 |
| 19. Preservative | q.s. |
| 20. Perfume | q.s. |

[Production Method]
(1) Components 9 to 19 are dissolved under heat at 90° C.
(2) Components 1 to 8 are added to (1) and uniformly dispersed with a roller.
(3) Component 20 is added to (2) and dissolved at 80° C., and the mixture is charged into a metal dish. An oily solid foundation was thus obtained.

[Results]
The oily solid foundation of the Example showed smooth touch during application as well as good adhesion to skin, and excellent in the uniformity of cosmetic-film and the cosmetic retentivity.

Example 15

Powdery Face Powder

| (Components) | (%) |
|---|---|
| 1. Mica of Production Example 3 | 20.0 |
| 2. Talc of Production Example 3 | Balance |
| 3. Mica titanium | 10.0 |
| 4. Red No. 226 | 0.5 |
| 5. Liquid paraffin | 0.5 |
| 6. Glyceryl tri(2-ethylhexanoate) | 1.0 |
| 7. Preservative | q.s. |
| 8. Perfume | q.s. |

[Production Method]
(1) Components 1 to 4 are uniformly mixed.
(2) Components 5 to 8 are added to (1) while stirring (1) with a Henschel mixer and the mixture is uniformly mixed.
(3) (2) is pulverized with a pulverizer. A face powder was thus obtained.

[Results]
The powdery face powder of the Example showed smooth touch during application as well as good adhesion to skin, and was excellent in the uniformity of cosmetic-film and the cosmetic retentivity.

Example 16

W/O Sunscreen Agent

| (Components) | (%) |
|---|---|
| 1. Fine particle zinc oxide | 2.0 |
| 2. Fine particle titanium oxide of Production Example 1 | 5.0 |
| 3. Glyceryl tri(caprylate/caprate) | 5.0 |
| 4. Bis-ethylhexyloxyphenol methoxyphenyl triazine | 3.0 |
| 5. Octyl palmitate | 3.0 |
| 6. 2-Ethylhexyl p-methoxycinnamate | 10.0 |
| 7. Methylene bis-benzotriazoryl tetramethylbutylphenol | 5.0 |
| 8. Decamethylcyclopentasiloxane | 10.0 |
| 9. Methyl polysiloxane/cetyl methyl polysiloxane/poly(oxyethylne/oxypropylene) methyl polysiloxane copolymer (Note 1) | 1.8 |
| 10. Glyceryl tri(2-ethylhexanoate) | 3.0 |
| 11. Preservative | q.s. |
| 12. Sodium chloride | 0.3 |
| 13. Purified water | Balance |
| 14. Dipropylene glycol | 3.0 |
| 15. Ethanol | 3.0 |
| 16. Perfume | q.s. |

(Note 1)
ABIL EM-90 (manufactured by EVONIC GOLDSCHMIDT GMBH)

[Production Method]
(1) Components 3 and 4 are dissolved with mild heat, then Components 1 and 2 are added thereto and the mixture is uniformly dispersed with a triple roller.
(2) Components 5 toll are dissolved at 70° C., then (1) is added thereto at 60° C., and the mixture is uniformly mixed and dissolved.
(3) Components 12 to 14 are mixed and dissolved, and then added to (2) at 60° C., and the mixture is emulsified.

(4) Components 15 and 16 are added to (3) and the mixture is uniformly mixed. A W/O sunscreen agent was thus obtained.

[Results]

The W/O sunscreen agent of the Example showed smooth touch during application as well as good adhesion to skin, and was excellent in the uniformity of cosmetic-film and the cosmetic retentivity.

Example 17

Solid Powdery Foundation

| (Components) | (%) |
|---|---|
| 1. Mica | 20.0 |
| 2. Talc | 15.0 |
| 3. Theanine(5%)-treated titanium oxide of Production Example 5 | 15.0 |
| 4. Sericite | Balance |
| 5. Theanine(2%)-treated yellow iron oxide of Production Example 5 | 2.0 |
| 6. Theanine(2%)-treated red iron oxide of Production Example 5 | 0.5 |
| 7. Theanine(2%)-treated black iron oxide of Production Example 5 | 0.2 |
| 8. Synthetic gold mica | 5.0 |
| 9. Crosslinking silicone/network silicone block copolymer | 1.0 |
| 10. Preservative | q.s. |
| 11. Boron nitride | 5.0 |
| 12. Polyethylene powder | 5.0 |
| 13. PET Resin powder | 3.0 |
| 14. Poly(methyl methacrylate) powder | 5.0 |
| 15. Liquid paraffin | 3.0 |
| 16. Dimethyl polysiloxane (10 mm$^2$/s: 25° C.) | 3.0 |
| 17. Cetyl 2-ethylhexanoate | 3.0 |
| 18. Perfume | q.s. |

[Production Method]
(1) Components 1 to 14 are uniformly dispersed at 75° C. with a Henschel mixer (manufactured by Mitsui Miike Machinery).
(2) Components 15 to 18 are uniformly mixed and dissolved.
(3) (2) is added to (1) and uniformly dispersed while stirring (1) with a Henschel mixer.
(4) (3) is pulverized with a pulverizer.
(5) (4) is charged in a metal dish and molded with compaction. A solid powdery foundation was thus obtained.

[Results]

The solid powdery foundation of the Example showed smooth touch during application, good compatibility with skin, uniform cosmetic-film, and beautiful finishing, and was excellent in no-color transfer to a face mask.

Example 18

Solid Powdery Eyeshadow

| (Components) | (%) |
|---|---|
| 1. Synthetic gold mica | 10.0 |
| 2. Theanine(2%)-treated talc of Production Example 5 | Balance |
| 3. Titanium oxide-coated mica | 30.0 |
| 4. Boron nitride | 5.0 |
| 5. Polyethyleneterephthalate/aluminum/epoxy laminated powder | 5.0 |
| 6. Ultramarine blue | 2.0 |
| 7. Red No. 202 | 0.5 |
| 8. Organopolysiloxane elastomer powder | 1.0 |
| 9. Preservative | q.s. |
| 10. Bismuth oxychloride | 5.0 |
| 11. Barium sulfate | 3.0 |
| 12. Liquid paraffin | 3.0 |
| 13. Dimethyl polysiloxane (6 mm$^2$/s: 25° C.) | 5.0 |
| 14. Diisostearyl malate | 3.0 |
| 15. Perfume | q.s. |

[Production Method]
(1) Components 1 to 11 are uniformly dispersed with a Henschel mixer (manufactured by Mitsui Miike Machinery).
(2) Components 12 to 15 are uniformly mixed.
(3) (2) is added to (1) and uniformly dispersed while stirring (1) with a Henschel mixer.
(4) (3) is pulverized with a pulverizer.
(5) (4) is charged in a metal dish and molded with compaction. A solid powdery eyeshadow was thus obtained.

[Results]

The solid powdery eyeshadow of the Example showed smooth touch during application as well as good compatibility with skin, and was excellent in the uniformity of cosmetic-film, the cosmetic retentivity, and the secondary adhesion-less effect.

Example 19

Solid Powdery Face Color

| (Components) | (%) |
|---|---|
| 1. Theanine(2%)-treated mica of Production Example 5 | 20.0 |
| 2. Theanine(2%)-treated talc of Production Example 5 | Balance |
| 3. Titanium oxide-coated mica | 10.0 |
| 4. Ultramarine blue | 0.5 |
| 5. Red No. 226 | 0.2 |
| 6. Polystyrene powder | 1.0 |
| 7. Preservative | q.s. |
| 8. Squalane | 2.0 |
| 9. Dimethyl polysiloxane (6 mm$^2$/s: 25° C.) | 3.0 |
| 10. Glyceryl 2-ethylhexanoate | 3.0 |
| 11. Perfume | q.s. |

[Production Method]
(1) Components 1 to 7 are uniformly dispersed with a Henschel mixer (manufactured by Mitsui Miike Machinery).
(2) Components 8 to 10 are uniformly mixed.
(3) (2) and component 11 are added to (1) and uniformly dispersed while stirring (1) with a Henschel mixer.
(4) (3) is pulverized with a pulverizer.
(5) (4) is charged in a metal dish and molded with compaction. A solid powdery face color was thus obtained.

[Results]

The solid powdery face color of the Example showed smooth touch during application as well as good compatibility with skin, and was excellent in the uniformity of cosmetic-film, the cosmetic retentivity, and the secondary adhesion-less effect.

Example 20

Powdery Face Powder

| (Components) | (%) |
| --- | --- |
| 1. Theanine(2%)-treated mica of Production Example 5 | 20.0 |
| 2. Talc | Balance |
| 3. Theanine(2%)-treated titanium oxide mica of Production Example 5 | 10.0 |
| 4. Crystalline cellulose powder | 5.0 |
| 5. Red No. 226 | 0.5 |
| 6. Liquid paraffin | 0.5 |
| 7. Glyceryl tri(2-ethylhexanoate) | 1.0 |
| 8. Preservative | q.s. |
| 9. Perfume | q.s. |

[Production Method]
(1) Components 1 to 5 are uniformly dispersed with a Henschel mixer (manufactured by Mitsui Miike Machinery).
(2) Components 6 to 9 are uniformly mixed.
(3) (2) is added to (1) while stirring (1) with a Henschel mixer and the mixture is uniformly mixed.
(4) (3) is pulverized with a pulverizer. A face powder was thus obtained.

[Results]
The powdery face powder of the Example showed smooth touch during application as well as good compatibility with skin, and was excellent in the uniformity of cosmetic-film, the cosmetic retentivity, and the secondary adhesion-less effect.

Example 21

Foundation

| (Components) | (%) |
| --- | --- |
| 1. Titanium oxide | 10 |
| 2. Sericite | Balance |
| 3. Theanine(2%)-treated talc of Production Example 5 | 10 |
| 4. Barium sulfate | 5 |
| 5. Silicic acid anhydride | 3 |
| 6. Sphere polystyrene | 3 |
| 7. Perfluorohexylethyltriethoxysilane-treated colcothar* | 0.5 |
| 8. Perfluorohexylethyltriethoxysilane-treated yellow iron oxide* | 2 |
| 9. Perfluorohexylethyltriethoxysilane-treated black iron oxide* | 0.2 |
| 10. Fine zinc white | 2 |
| 11. Cetyl 2-ethylhexanoate | 8 |
| 12. Petrolatum | 1 |
| 13. Liquid paraffin | 3 |
| 14. Perfume | 0.1 |

*3%-Treated with Dynasylan F8261 (manufactured by Degussa Japan)

[Production Method]
(1) Components 11 to 14 are mildly heated to 70° C., mixed and dissolved.
(2) Components 1 to 10 are uniformly mixed with stirring.
(3) (1) is added to (2) and the mixture is uniformly mixed with stirring.
(4) 100 parts by mass of a 5% ethanol aqueous solution is added as a solvent to 100 parts by mass of (3), and the mixture is uniformly mixed with stirring to obtain a slurry.
(5) (4) is charged in a dish container, and paper for absorbing solvent is disposed between the cosmetic preparation and a compaction head, and compaction molding is performed while absorbing the solvent added.
(6) (5) is dried at room temperature for 10 hours. A foundation was thus obtained.

[Results]
The foundation of the Example showed smooth touch during application as well as good compatibility with skin, and was excellent in the uniformity of cosmetic-film, the cosmetic retentivity, and the secondary adhesion-less effect.

Example 22

Eyeshadow

| (Components) | (%) |
| --- | --- |
| 1. Syntehtic gold mica | 10.0 |
| 2. Theanine(2%)-treated talc of Production Example 5 | Balance |
| 3. Titanium oxide-coated mica | 30.0 |
| 4. Boron nitride | 5.0 |
| 5. Polyethyleneterephthalate/aluminum/epoxy laminated powder | 5.0 |
| 6. Theanine(2%)-treated red iron oxide of Production Example 5 | 1.0 |
| 7. Red No. 202 | 1.5 |
| 8. Organopolysiloxane elastomer powder | 1.0 |
| 9. Preservative | q.s. |
| 10. Bismuth oxychloride | 5.0 |
| 11. Barium sulfate | 3.0 |
| 12. Liquid paraffin | 5.0 |
| 13. Dimethyl polysiloxane (6 mm$^2$/s; 25° C.) | 5.0 |
| 14. Perfume | q.s. |

[Production Method]
(1) Components 1 to 11 are uniformly mixed with stirring.
(2) Components 12 to 14 are uniformly mixed.
(2) (2) is added to (1) and uniformly mixed with stirring.
(3) 30 parts by mass of light liquid isoparaffin is added as a solvent to 100 parts by mass of (2) and the mixture is uniformly mixed with stirring to obtain a slurry.
(5) (4) is charged in a dish container, and paper for absorbing solvent is disposed between the cosmetic preparation and a compaction head, and compaction molding is performed while absorbing the solvent added.
(6) (5) is dried at room temperature for 10 hours. An eyeshadow was thus obtained.

[Results]
The eyeshadow of the Example showed smooth touch during application as well as good compatibility with skin, and was excellent in the uniformity of cosmetic-film, the cosmetic retentivity, and the secondary adhesion-less effect.

The invention claimed is:
1. A powder comprising:
at least one type of powder particles and
from 0.1 to 5% by mass of theanine;
wherein only the theanine is present on the surface of the powder particles.
2. The powder according to claim 1, wherein the at least one type of the powder particles are at least one selected from the group consisting of inorganic powder particles, photoluminescent inorganic powder particles, and complex inorganic powder particles.
3. A cosmetic preparation comprising the powder according to claim 1.
4. The cosmetic preparation according to claim 3 that comprises from 0.1 to 90% by mass of the powder particles.
5. The powder according to claim 1, wherein the at least one type of the powder particles comprises at least one type of inorganic powder particles selected from the group consisting of particles of titanium oxide, black titanium oxide, iron blue pigment, ultramarine blue, colcothar, yellow iron oxide, black iron oxide, zinc oxide, aluminum oxide, silica, magnesium oxide, zirconium oxide, magnesium carbonate, calcium carbonate, chromium oxide, chromium hydroxide, carbon black, aluminum silicate, magnesium silicate, aluminum magnesium silicate, mica, synthetic mica, sericite, talc, kaolin, silicon carbide, barium sulfate, bentonite, smectite, and boron nitride.

6. A cosmetic comprising the powder according to claim 1, wherein said cosmetic is selected from the group consisting of a foundation, a concealer, a face powder, an eyeshadow, a cheek rouge, a makeup base, an eye color, a rouge, an eyebrow, a mascara, an eyeliner, a manicure, and a sun screen cosmetic preparation.

7. The powder according to claim 1, wherein the at least one type of the powder particles comprises inorganic powder particles and the theanine has been applied to the surface of the inorganic powder particles by treating the inorganic powder particles in a solvent comprising theanine.

8. The powder according to claim 1, wherein the at least one type of the powder particles comprises inorganic powder particles and the theanine has been applied to the surface of the inorganic powder particles by treating the inorganic powder particles in a gas phase.

9. The powder according to claim 1, wherein the at least one type of the powder particles comprises inorganic powder particles and the theanine has been applied to the surface of the inorganic powder particles by pulverization with mixing and sheer.

10. A powdery cosmetic preparation comprising inorganic powder particles that have been surface-treated with theanine, and an organic powder, wherein only the theanine is present on the surface of the inorganic powder particles.

11. The powdery cosmetic preparation according to claim 10, wherein a content of the inorganic powder surface-treated with theanine in the powdery cosmetic preparation is from 0.1 to 90% by mass.

12. The powdery cosmetic preparation according to claim 10, wherein the organic powder is at least one selected from the group consisting of a nylon powder, a poly(methyl methacrylate) powder, a crystalline cellulose powder, and a vinyl dimethicone/methicone silsesquioxane crosspolymer powder.

13. The powdery cosmetic preparation according to claim 10, wherein a content of the organic powder in the powdery cosmetic preparation is from 0.1 to 30% by mass.

14. The powdery cosmetic preparation according to claim 10, further comprising boron nitride.

15. The powdery cosmetic preparation according to claim 10, further comprising from 0.1 to 30% by mass boron nitride.

16. The powdery cosmetic preparation according to claim 10,
wherein the inorganic powder particles that have been surface-treated with theanine are at least one of titanium oxide, iron oxide, talc, mica, and sericite,
wherein the organic powder is at least one selected from the group consisting of a nylon powder, a poly(methyl methacrylate) powder, a crystalline cellulose powder, and a vinyl dimethicone/methicone silsesquioxane crosspolymer powder, and
wherein the powdery cosmetic preparation further comprises from 0.1 to 30% by mass boron nitride.

17. A method for producing the powder according to claim 1 comprising applying theanine to the surface of inorganic particles.

18. A method for cosmetically treating skin comprising applying the powder according to claim 1 to skin.

* * * * *